(12) United States Patent
Keeping et al.

(10) Patent No.: US 6,787,106 B2
(45) Date of Patent: Sep. 7, 2004

(54) ANALYSIS DEVICE (75) Inventors: Sean Crispian Keeping, Shortlands (GB); Dieter Binz, Strease (DE); Albrecht Vogel, Stutensee (DE)

(73) Assignee: ABB Automation Limited, Stevenage (GB)

( * ) Notice: Subject to any disclaimer, the term of this patent is extended or adjusted under 35 U.S.C. 154(b) by 326 days.

(21) Appl. No.: 09/867,741

(22) Filed: May 31, 2001

(65) Prior Publication Data

US 2002/0054828 A1 May 9, 2002

(30) Foreign Application Priority Data

May 31, 2000 (GB) .............................................. 0013215

(51) Int. Cl.$^7$ ........................ G01N 21/00; G01N 31/22; G01N 15/06; G01N 33/00; G01N 33/48
(52) U.S. Cl. ............................ 422/50; 422/58; 422/61; 422/62; 422/68.1; 422/79; 422/81; 422/82.04; 436/43; 436/164; 436/165; 436/174; 436/177; 436/178; 73/1.01; 73/1.02; 73/19.01; 73/23.2; 73/53.01
(58) Field of Search .............................. 422/50, 58, 61, 422/62, 68.1, 79, 81, 82.04; 436/43, 164, 165, 174, 177, 178; 73/1.01, 1.02, 19.01, 23.2, 53.01

(56) References Cited

U.S. PATENT DOCUMENTS

| | | | | |
|---|---|---|---|---|
| 3,839,902 | A | | 10/1974 | Scott |
| 4,089,209 | A | | 5/1978 | Grana et al. |
| 4,166,392 | A | * | 9/1979 | Farnworth ................ 73/863.31 |
| 4,769,974 | A | * | 9/1988 | Davis .......................... 53/433 |
| 6,187,530 | B1 | * | 2/2001 | Scholin et al. .................. 435/4 |
| 6,197,256 | B1 | | 3/2001 | Siepmann |

FOREIGN PATENT DOCUMENTS

| | | |
|---|---|---|
| WO | 93/17334 | 9/1993 |
| WO | WO 93/17334 | 9/1993 |
| WO | 97/21088 | 6/1997 |
| WO | 99/18421 | 4/1999 |
| WO | WO 99/18421 | 4/1999 |

* cited by examiner

Primary Examiner—Jill Warden
Assistant Examiner—Brian Sines
(74) Attorney, Agent, or Firm—Stites & Harbison PLLC; Ross F. Hunt, Jr.

(57) ABSTRACT

An analysis device, preferably in the form of a floating buoy, is disclosed for the analysis of fluids, such as waste water. The device has a main body portion and a removable cartridge containing consumable ingredients for use in analysis.

34 Claims, 8 Drawing Sheets

ANALYSIS DEVICE

The present invention relates to analysis of fluids, more particularly, but not exclusively, to a unit for analysis of waste water.

Where the storage of quantities of liquid or semi-liquid effluent is concerned, periodic monitoring is desirable for a number of reasons, in particular, public health. To date this has been achieved by the taking of a sample by a technician for subsequent analysis in a laboratory. This process has the disadvantages that it is labour intensive, expensive and prone to human error.

The present invention addresses the above mentioned problems by the provision of an automatic analysis unit.

A particular concern of the invention is to provide an analysis unit wherein the reagents used in the analysis process can be easily replaced. Aspects and preferred features of the invention are set Out in the claims to which reference should be made.

In an embodiment the present invention provides an analysis device comprising a main body part and a cartridge part: the main body part being adapted for positioning in a fluid to be analyzed and including analysis means; and the cartridge part including means for extracting a sample from the fluid; means for storing at least one reagent and means for transferring the sample and the at least one reagent to the analysis means so as to permit analysis of the sample. As an alternative to transferring the fluid to analysis means in the main body part, the fluid may be retained in the cartridge and partially analysed and signals from analysis devices mounted in the cartridge may be transferred to the main body part.

Although the device may be rigidly mounted to a wall or container for the fluid, and preferably means are provided for suspending the device in the fluid, preferably so that a sampling inlet is at a substantially fixed depth with respect to the fluid surface (this may reduce the effects of variation in sample composition with depth, leading to more reliable readings as compared to a fixed sampling inlet). Most advantageously, the device is buoyant, preferably comprising a buoy; this may enable a compact device to be deployed in a relatively hostile or inaccessible environment without undue difficulty. The buoy will usually be arranged to be tethered and may include means for securing the buoy to a fixing location. The device will preferably also have means for receiving power and/or means for transmitting a signal or measurement; these may advantageously be communicated along a signaling cable. Most preferably, the device is coupled to a fixing point by tethering means, preferably a boom, which carries a signaling and/or power cable.

As an alternative, the device may signal by wireless means (for example radio (e.g. "bluetooth" protocol), infrared or ultrasound. The device may also receive power by wireless means, for example by inductive power transmission, microwave or laser radiation or may include sufficient power supplies (for example batteries or fuel cells, or mechanical power generators, for example to generate power from movement (e.g. wave motion)) to power the device for a period of time between maintenance operations. Thus, in certain applications, the device may comprise a substantially free-floating buoy, and may include motivation means for moving the buoy through the fluid. Such a device may also include means for obtaining a measure of position (for example a GPS receiver) and means for controlling the buoy to follow a pre-programmed or transmitted route; such a device may be particularly useful for monitoring fluid in a large reservoir. Where the device has a removable cartridge, the cartridge may contain an expendable power source, and the buoy may be periodically "summoned" back to a maintenance point for replacement of the cartridge.

In a preferred implementation, the invention provides an analysis device for analyzing a fluid comprising means for extracting a sample from the fluid, wherein the device comprises a buoy having onboard means for analyzing the fluid and means for communicating the results of the analysis to a remote location, the buoyancy of the buoy being such that the means for extracting a sample from the fluid is maintained substantially at a constant depth with respect to the fluid.

A further embodiment of the invention provides an analysis device comprising a main body part and a cartridge part which, in use, are mated wherein said main body part is adapted for positioning in a fluid to be analyzed and includes analysis means; and said cartridge part comprises means for extracting a sample from the fluid; wherein said buoy comprises means for transferring the sample from said extraction means to said analysis means so as to permit analysis of the sample, said means comprising a needle situate on one of the cartridge and main body part and corresponding needle receiving means situate on the other of the cartridge and main body part.

A further independent aim of the invention is to provide an analysis buoy which stores toxic waste produced in the analysis process and in which the toxic waste can be easily extracted for disposal.

An embodiment of the invention provides an analysis buoy comprising a main body part and a cartridge part which, in use, are mated wherein said main body part is adapted for positioning in a fluid to be analyzed and includes analysis means; and wherein said cartridge part comprises means for the storage of waste material after analysis and wherein said buoy comprises means for transferring the waste from said analysis means to said storage means.

A further independent aim of the invention is to provide an analysis buoy in which an analysis means having a relatively short lifetime such as a biological oxygen sensor can be easily replaced.

An embodiment of the invention provides an analysis buoy comprising a main body part and a cartridge part which, in use, are mated wherein said main body part is adapted for positioning in a fluid to be analyzed; and said cartridge part comprises means for analyzing said fluid.

The invention extends to cartridges for use in the above mentioned arrangements.

Aspects of the invention provide, independently, a cartridge for use with an analysis unit, preferably a buoy, comprising means for analysis of a fluid, the cartridge comprising any of the following or any combination of the following:

plurality of fluid coupling means, preferably in the form of needles or needle-receiving means, arranged to mate with complementary coupling means on the analysis unit for conveying fluid to be analysed or reagents between the cartridge and the analysis unit;

a supply of at least one reagent to be consumed by the analysis unit;

a waste container for storing waste produced by analysis;

means for extracting fluid to be analysed and filtering the fluid;

an analysis cell, for example a biosensor, containing ingredients, for example living micro-organisms, of limited lifetime;

a microprocessor and/or memory means for storing information about the history of the cartridge;

means for mating with the analysis unit arranged to expose fluid coupling means, preferably needles, on the cartridge when mated with the analysis unit and to protect the coupling means when the cartridge is removed from the analysis unit;

means for maintaining a substantially constant hydrostatic pressure for reagents contained within the cartridge;

pump means, preferably peristaltic pump means, for pumping fluid and air into and/or out of the analysis unit, the pump means being arranged to couple with a motor in the analysis unit a filter element for filtering fluid extracted from the fluid to be analysed, preferably located on the cartridge to be immersed in the fluid to be analysed.

An embodiment of the present invention will now be described by way of example only with reference to the accompanying drawings in which.

Figure 1:
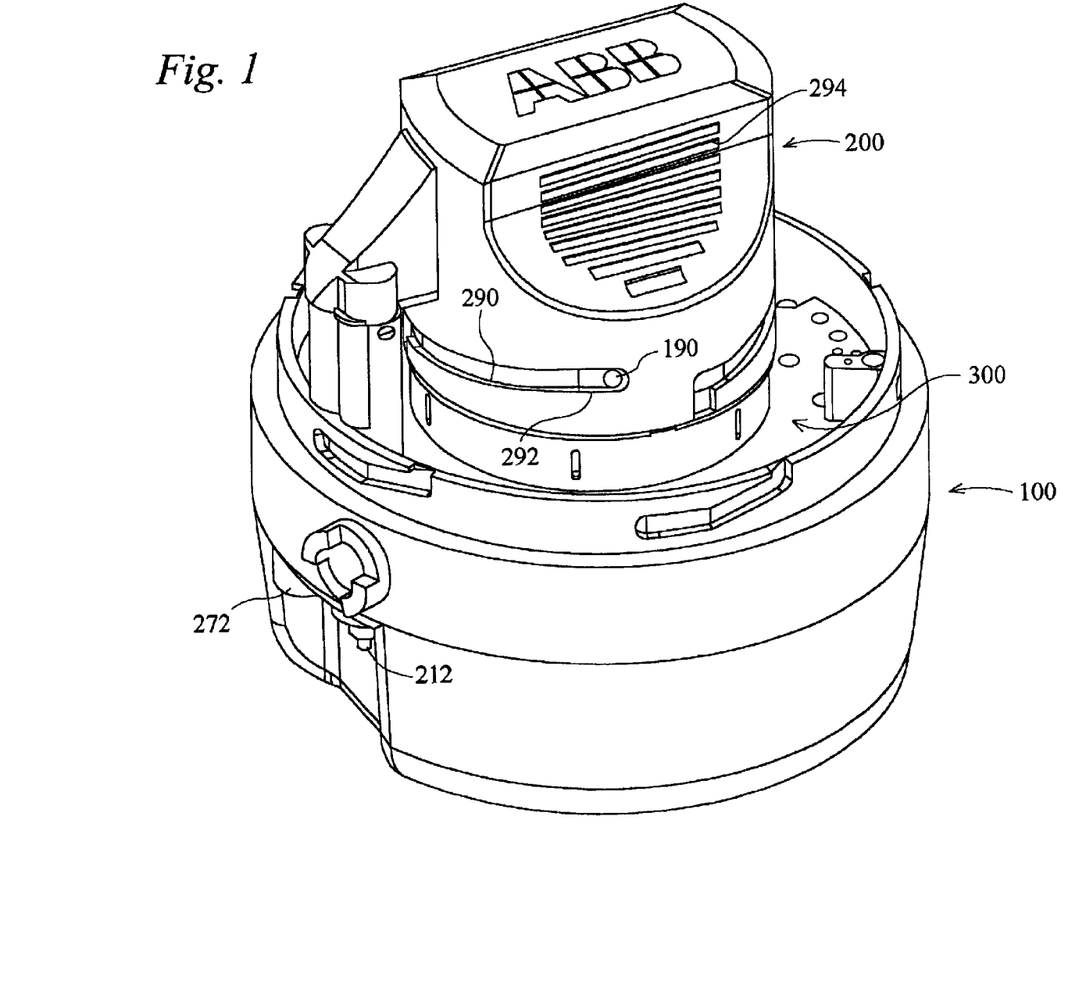
FIG. 1 shows diagrammatically an analysis buoy having a main unit and a detachable cartridge according to an embodiment of the invention.
Figure 2:
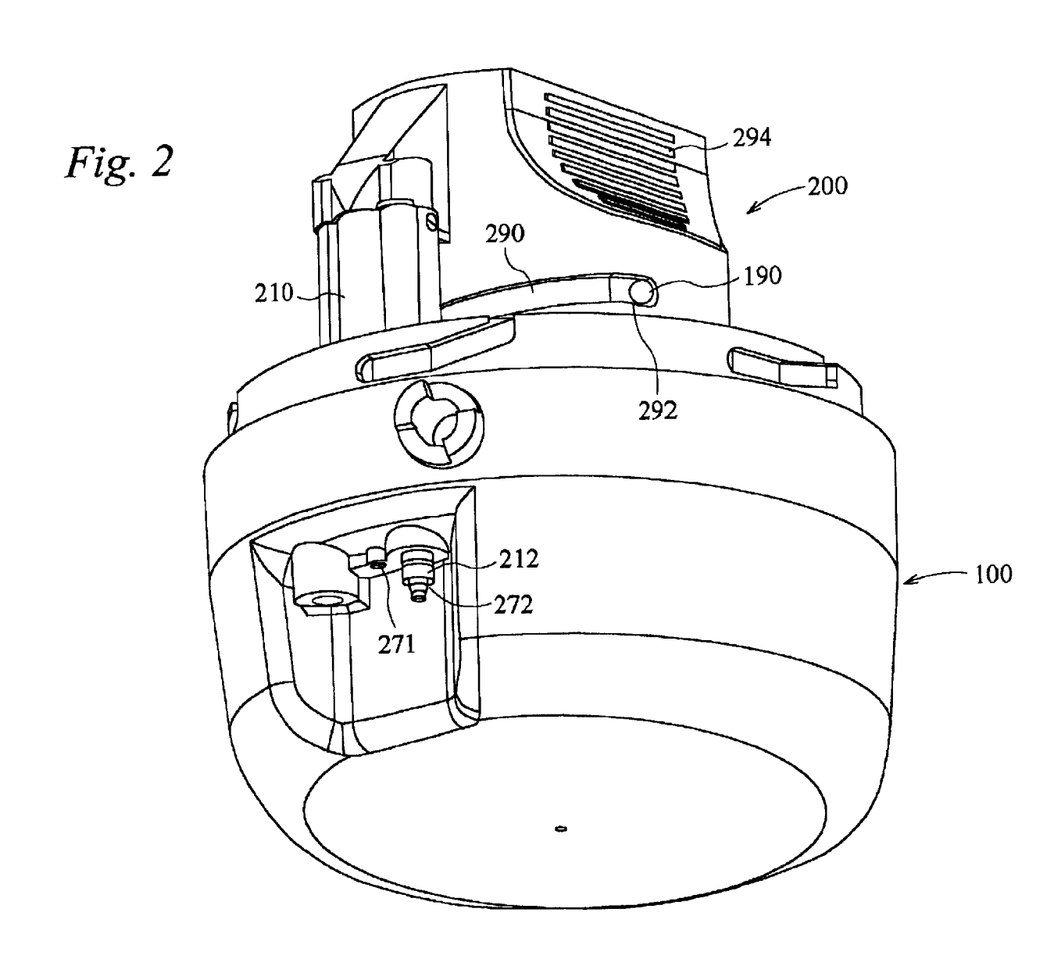
FIG. 2 shows diagrammatically an alternative view of the embodiment shown in FIG. 1.

FIGS. 1 and 2 show the overall arrangement of a buoy according to an embodiment of the invention. The buoy consists of two parts, the main body unit 100 and a detachable cartridge 200.

In the embodiment described below, the analysis wafer is located on the buoy and the reagents are located in a disposable (or more preferably recyclable) removable cartridge. In an alternative embodiment, the wafer is mounted in the cartridge and motors for driving discrete pumps are provided in the body of the buoy. Spindles for driving the pumps extend between the buoy and the cartridge, preferably through environmentally sealed apertures. In a preferred alternative implementation, the fluid is contained wholly within the cartridge and the control apparatus is provided in the buoy, so there is no liquid interface between the cartridge and the buoy.

It is to be noted that a number of preferred features of a cartridge and analysis device are described in the following. Unless otherwise stated, or specifically required by the context, such features may be independently provide, for example in a device in which an analysis wafer is located in the cartridge and communication with a main body component is "dry". More specifically, it will be appreciated of course that the liquid transferring means will not be applicable in such a case but all other features are applicable to a "dry" interface unless otherwise stated.

Although not shown in FIGS. 1 and 2, in overview, the main unit 100 contains an analysis wafer which conducts the analysis of the fluid together with a power unfit, motor and heating/cooling unit and controlling microprocessor. The cartridge 200 contains a probe and associated pump for supplying the sample for analysis to the main unit, stored reagents for use by the analysis wafer in analysis, a biological oxygen sensor and a controlling microprocessor.

The two parts are interlocked together by an interface mechanism generally designated 390 which comprises three circumferentially spaced radially extending studs 190 located on a locking ring provided on the main body 100 and three corresponding inclined slots 290 on the cartridge 200. The studs 190 locate in the respective slot 290 and ride up the slot 190 during a quarter turn of the locking ring relative to the cartridge 100 to locate in a flat 292 at the far end of the slot so as to secure the cartridge 200 to the main body 100. The lower portion of the cartridge 200 has a spring loaded bias as will be explained later. The main body 100 and cartridge 200 are provided with a keying mechanism (not shown) such that correct location between the two parts is ensured.

The cartridge 200, which will be described in greater detail below, is generally cylindrical in shape, its lower flat end being that adapted to mate with the main body 100. In the embodiment shown, the upper end is formed so as to provide a grip 294 to allow user manipulation. The cartridge includes probe body 210 which extends into sample probe 212 (which has a seal at the point where it passes through the body of the buoy) and waste outlet 272 which protrude from the body of the cartridge so as to extend through the main body 100 once the cartridge 200 and the main body 100 are mated. The cartridge 200 is typically 10 to 15 centimetres (cm) in height and its base typically has a diameter of 10 to 20 cm. A temperature sensor 271 for sensing the temperature of the sample to be analysed and a pressure sensor or other sensor (e.g. conductivity) for detecting that the buoy is actually in a sample (and approximately at the correct depth) may be provided, as an advantageous feature.

The main body 100 of the buoy is generally cylindrical in shape having typical dimensions of 30 to 50 centimetres diameter and a height of 25 to 50 cm. It has a cut away portion 295 which allows the protrusion of the cartridge probe 212 and waste outlet 272 when assembled. The buoyancy of the main unit is arranged such that, in use, it floats on the fluid with the cartridge probe 212 and waste outlet 272 extending into the fluid. The buoyancy of the main unit 100 may be fixed by the manufacturer by any conventional means but in a modification could be user adjustable so as to allow the user to adapt the unit for use in a variety of fluids having different densities.

The bodies of the main unit 100 and cartridge 200 may be constructed by moulding from a plastics material for ease of construction but may include one or more metal chassis members, preferably aluminum, for enhanced rigidity and improved thermal characteristics. The individual portions of the bodies may be heat welded together, this being an economical method of construction whilst ensuring that the units are water-tight.

Figure 3:
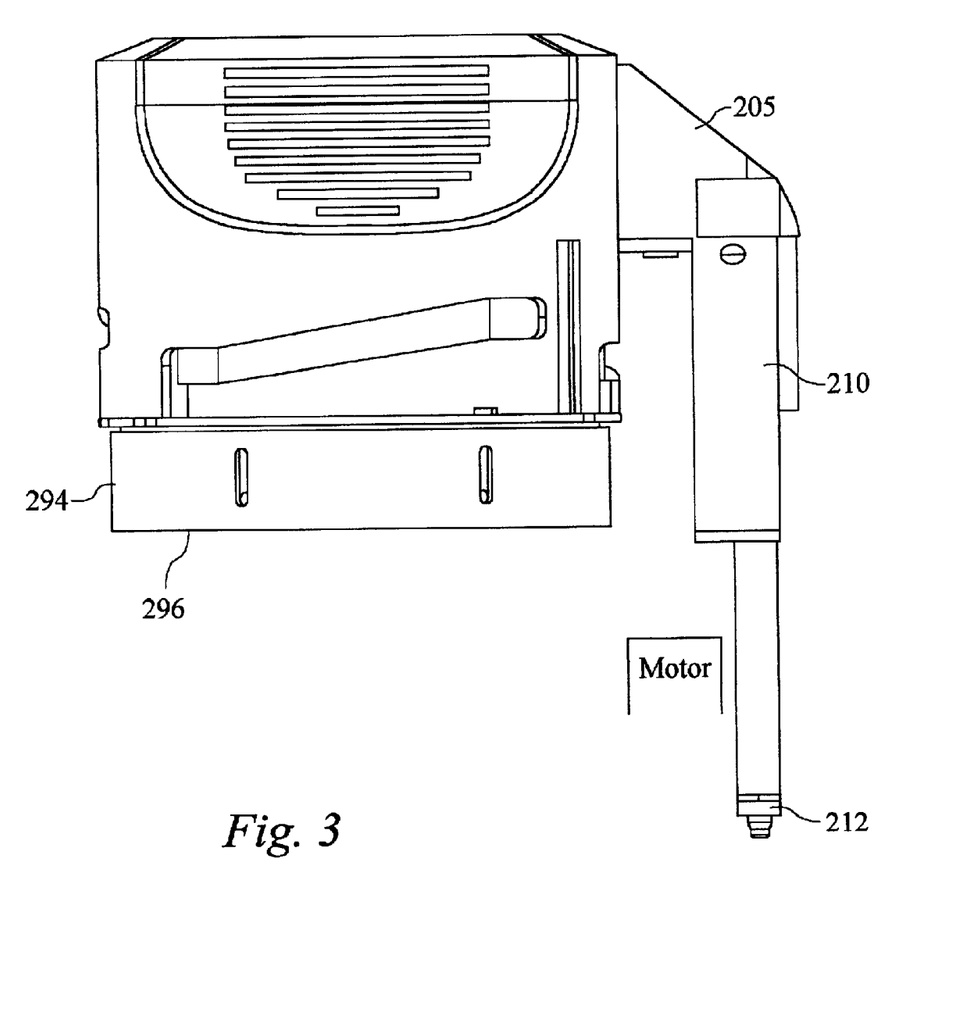
FIG. 3 shows diagrammatically the cartridge of the embodiment of the analysis buoy shown in FIG. 1.
Figure 4:
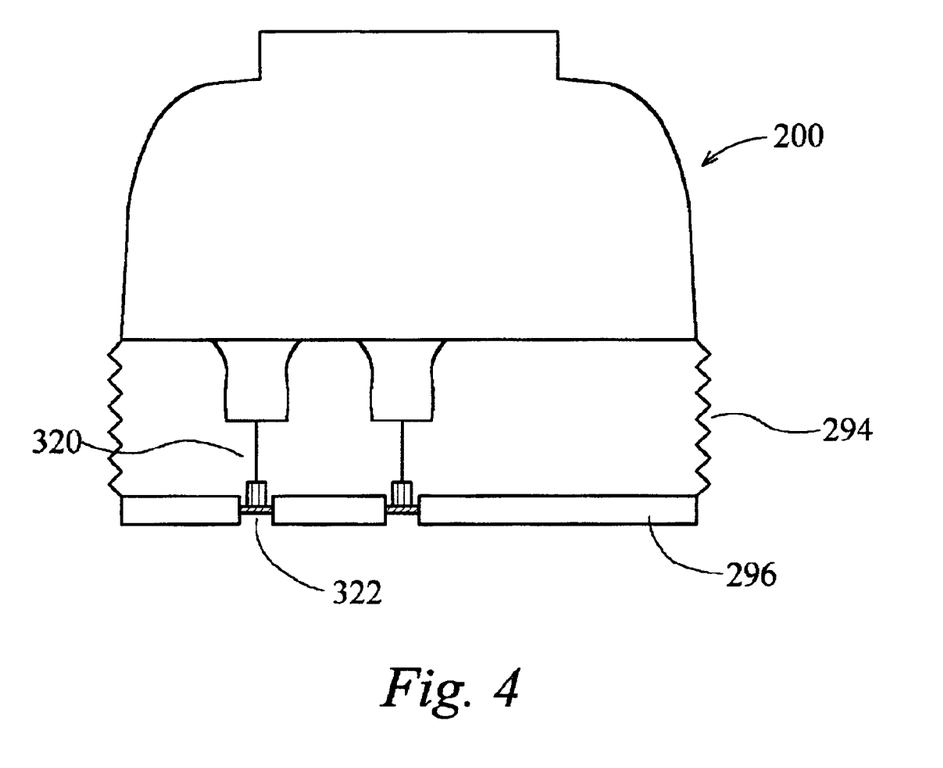
FIG. 4 is a schematic diagram of the cartridge of FIG. 3.
Figure 5:
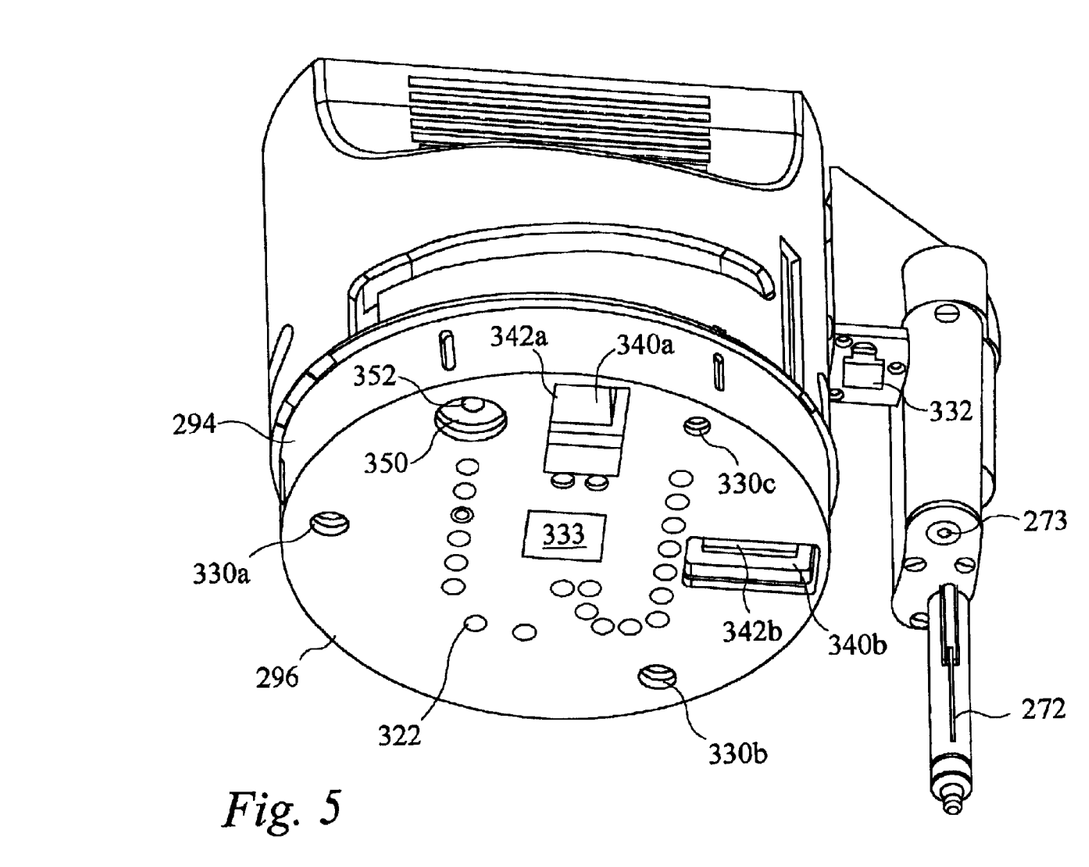
FIG. 5 is an alternative view of the cartridge shown in FIG. 3 showing, in particular, the baseplate.

FIGS. 3, 4 and 5 show the cartridge of the embodiment in greater detail, FIG. 4 being in diagrammatic form.

As will be seen from FIGS. 3 and 5, mount 205 projects radially from the body of the cartridge 200. From this extends, substantially parallel to the axis of the cylindrical body of the cartridge 200 and in the direction of the base of the cartridge 200, probe body 210 which extends into probe 212 and waste outlet 272.

The probe comprises a cylindrical section and tip and, preferably, incorporates a filter (not shown), more preferably a filter having a movable filter section as more particularly described in the Applicant's concurrently filed application Serial No. (attorney docket no. P07239US00 the entire disclosure of which is incorporated herein by reference. Such a movable filter section causes movement of the effective filtering portion over time, thus reducing the possibility of clogging. As shown, schematically in FIG. 3, a motor drive unit may be provided on the base unit for driving the moving filter assembly.

The waste outlet 272 axially extends along the same direction as the probe 210 and terminates in a waste orifice.

The mating portion is constructed of a retractable cylinder 294 and a baseplate 296. The baseplate 296 contains a plurality of apertures, the significance of which will be described in greater detail below. Upon mating of the cartridge 200, the baseplate 296 is forced to retract (upwards in the figure) such that needles 320 protrude from plural of the apertures 322. Prior to this mating procedure, these needle covering apertures 322 are sealed with a rubber or similar material and the baseplate 294 is spring biased towards this position. The aperture covering material is preferably re-sealable, such that, upon removal of the cartridge 200, the baseplate 294 moves under its spring bias to its extended position and the apertures 322 are again sealed. A seal (not shown) is provided to ensure fluid tightness around the retractable baseplate 296.

With particular reference to FIG. 5, it will be seen that in the embodiment there are about twenty of these needle (typically at least 5 or more typically at least about 10, typically up to about 30) covering apertures 322 arranged in a spaced apart pattern over the baseplate 296.

In addition to these apertures there is an aperture 350 containing a coil coupling 352 for supplying power by means of an inductive coupling to the cartridge and also for communicating data between the cartridge and buoy. Conventional inductive power and data coupling circuitry may be employed. In the embodiment so called contactless power connections are used which operate using the principle of induction as the reliability of such contacts compensates for the sacrifice in efficiency. However, less preferably, power connections that make mechanical contact could be utilised instead.

Recesses 330a, 330b, 330c are provided for mounting protrusions on the base to mate with to provide positive seating of the cartridge.

To drive the filter assembly, as discussed elsewhere, a the rotational drive coupling 273, is provided the purpose of which will be explained later. The coupling method used in the embodiment is that known as a dog clutch although any suitable mechanical coupling capable of torque transmission could be used. A seal (not shown) may be provided around the driven member so as to ensure fluid tightness. If mechanical pumps are provided in the cartridge, these may be driven by motors in the main body part in a similar manner.

There are further provided apertures 340a, 340b, in which are provided thermally conductive blocks 342a, 342b. These are arranged to make thermal contact with corresponding blocks on the main unit 100. The purpose of these blocks is explained below. In addition, a recess 332 for receiving a heat source for debubbling of the fluid entering the cartridge from the filter may be provided.

The previously described retraction movement of the baseplate is such that the coil coupling member 352, the thermally conductive blocks 342a, 342b and the power connections 332a, 332b, 332c become exposed upon movement of the baseplate 296 toward the body portion of cartridge 200 that is to say during mating of the cartridge 200 with the main unit 100. In this manner, reliable interfacing of the various components is achieved whilst they are protected upon disengagement of the cartridge 200. It will be appreciated that suitable seals are provided around each of the interface components within the apertures such as to maintain fluid tightness. Also, a foam or other compressible pad 333 may be provided which is soaked in sterilising solution and arranged so that a small amount of solution is released upon engagement of the cartridge, to sterilize the surfaces.

Figure 6:
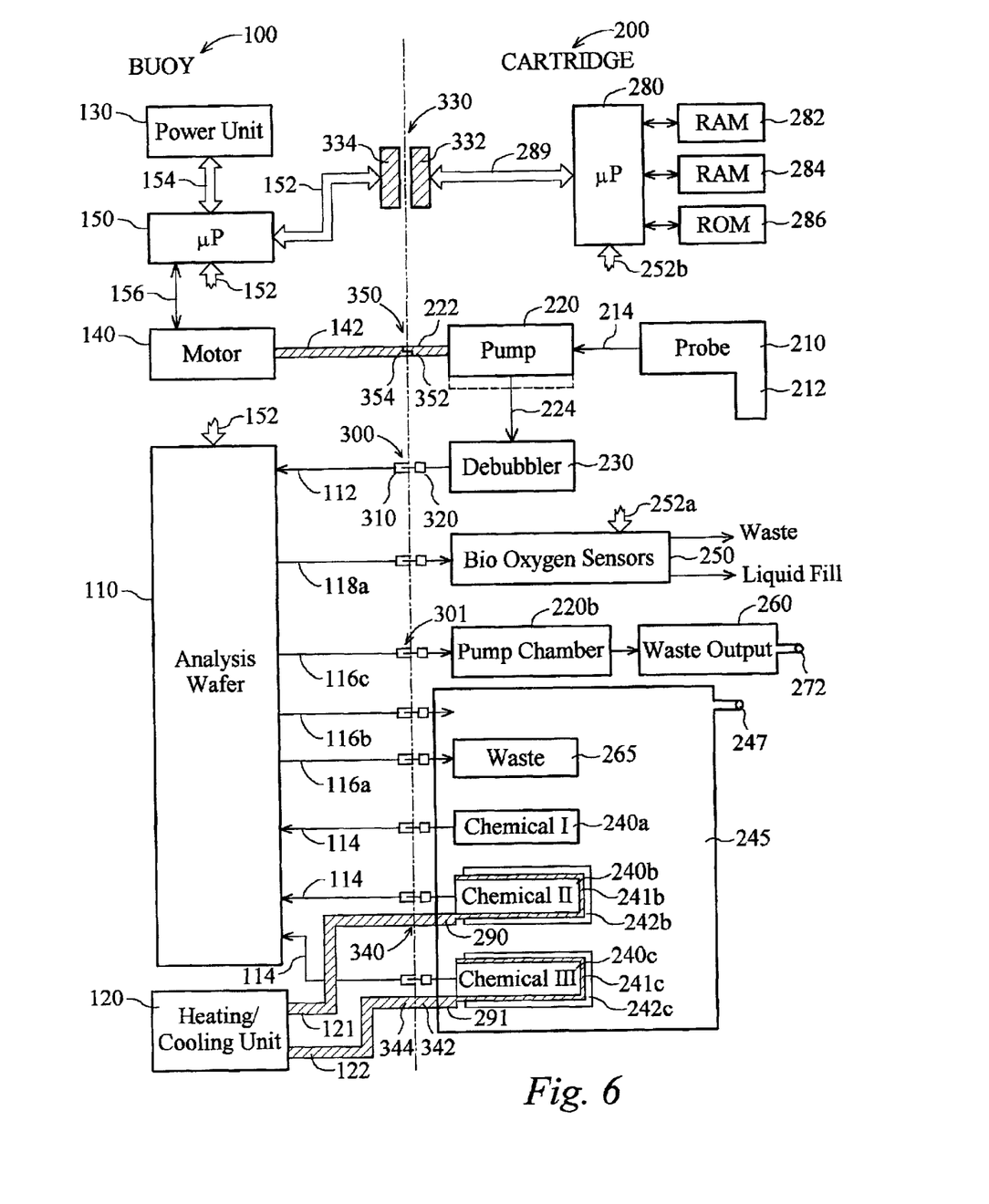
FIG. 6 is a block diagram showing the principal parts of an analysis buoy according to the invention and the interaction therebetween.

The overall operation of the unit will now be explained with reference to FIG. 6.

The constituents of the main body 100 will first be described.

As will be seen form the figure, predominantly analysis occurs in analysis wafer 110. Analysis wafer 110, the detail of which is not shown, contains chambers wherein reactions between chemical reagents and a fluid sample can be carried out together with associated analysing electronics. The wafer carries out a fluid switching operation which allows an input sample (or fluid generally) to be directed in various manners. Fluid is pumped around the wafer using micropumps driven by piezoelectric elements (which may be on the wafer itself, or arranged to bear on the wafer. Alternatively, discrete mechanical pumps may be provided, preferably (but not necessarily) driven by means of motors mounted in the main body part, by means of a rotational coupling. The wafer may be of any suitable material and may comprise a silicon or glass substrate or it may be formed from plastics material. In a development, not shown, the wafer may be formed as part of the disposable cartridge, with driving devices mounted in the base of the buoy.

The analysis wafer contains plural fluid inputs and outputs. In particular the sample to be analysed is provided on sample input 112. The reagents employed for the analysis are input via plural reagent inputs 114, three of which are shown in the figure. In the embodiment, inputs for twelve reagents are provided although modification of the number of such inputs could be made dependent upon the complexity of the substance to be analysed and the extent of analysis desired. Three waste outputs 116a, 116b, 116c are provided from the analysis wafer. The first waste output 116a contains toxic waste, the second waste output 116b contains hazardous waste being that which is of a lower toxicity than the toxic waste nonetheless is not suitable for exhaust from the buoy. The third waste output 116c contains waste suitable for exhaust from the buoy. Waste products are routed internally in the wafer to the appropriate waste output. In the embodiment, the analysis wafer has an additional output port 118a. The additional output port 118a allows a sample to be routed to an analysis unit external to the analysis wafer 110. Optionally an additional input port may allow waste to be returned from the external analysis unit so that it can be routed by the analysis wafer 100 to an appropriate waste output 116. In the embodiment the additional analysis unit is biological oxygen sensor 250 which is provided in the cartridge 200.

The analysis wafer acts under the control of microprocessor 150 which has associated ROM and RAM (not shown) via data bus 252, part of which only is shown.

The main unit 100 additionally contains power supply 130 for providing power to the unit. In the embodiment, the power unit is connected to a remote power supply via a cable (not shown). In the embodiment, analysis data is also passed along this cable although in a modification a separate cable could be employed. Data is passed between the power unit and the microprocessor via data bus 152.

Also contained within the main unit 100 is motor 140 which is powered from the power supply 130 under the control of microprocessor 150 via control line 156, which in the embodiment is bidirectional so that feedback can be provided from the motor 140. The motor 140 provides rotational drive via drive member 142 and coupling 354 to the cartridge 200 as will be more fully described below.

Further contained in the main unit is heating/cooling unit 120 which, in the embodiment, is comprised of plural Peltier elements. In the embodiment, two outputs are provided, as shown in the figure, but more or fewer may be provided as required. The outputs are effectively maintained at a constant predetermined temperature under the control of the microprocessor 150 via data bus 158 only part of which is shown.

These outputs are effective to transfer heat both to and from elements in the cartridge (to be described) via thermally conductive paths 121, 122.

The constituent parts of the cartridge 200 will now be described.

The cartridge contains microprocessor 280 together with associated RAM 282, ROM 286 and non-volatile RAM 284. The microprocessor is effective to control the constituent parts of the cartridge on the basis of commands stored in ROM 286. ROM 286 further contains identification information which includes the type of cartridge, the composition and amount of the reagents in the cartridge (to be described) and details of any analysis units contained within the cartridge 200. Non-volatile RAM 284, which may be so-called flash RAM is provided as a backup storage allowing full processing of the analysis results upon replacement of the cartridge. RAM 282 is used by the microprocessor 280 for general storage purposes. History and identification information may be stored, enabling the history of the cartridge and its authenticity to be verified. Data may be stored for logging, testing and calibration purposes, in particular data may be logged in the cartridge for analysis by the cartridge recycler off-line to determine potential faults or to evaluate performance, in addition to the information made available to the user.

The microprocessor 280 communicates with that provided in the main unit 100 via data link 289 and contactless power connection 352, the data being encoded such that power transmission and data transmission can occur via the same contactless interface 352. This is a preferable feature of the embodiment and in a modification, separate electrical connectors could be used.

As previously described, probe tip 212 extends from the cartridge 200 so as to extract a fluid sample. The probe tip 212 is thereafter connected via probe body 210 and pipe 214 to a first chamber 220a of peristaltic pump 220. The pump 220 is driven via driven shaft 222 which is in turn driven by the motor 140 in the main body 100 of the buoy. Hence the necessity of providing a relatively heavy, expensive and low maintenance component in the replaceable cartridge is obviated.

From the pump chamber of the peristaltic pump 220a, the sample is thereafter pumped via pipe 224 to debubbler 230 which is effective to eliminate excess dissolved air from the sample. The sample is then provided to the main body 100, more particularly the analysis wafer 110, via fluid interface 300 comprising needle 320 in the cartridge 200 and needle receiver 310 in the main body.

Figure 7:
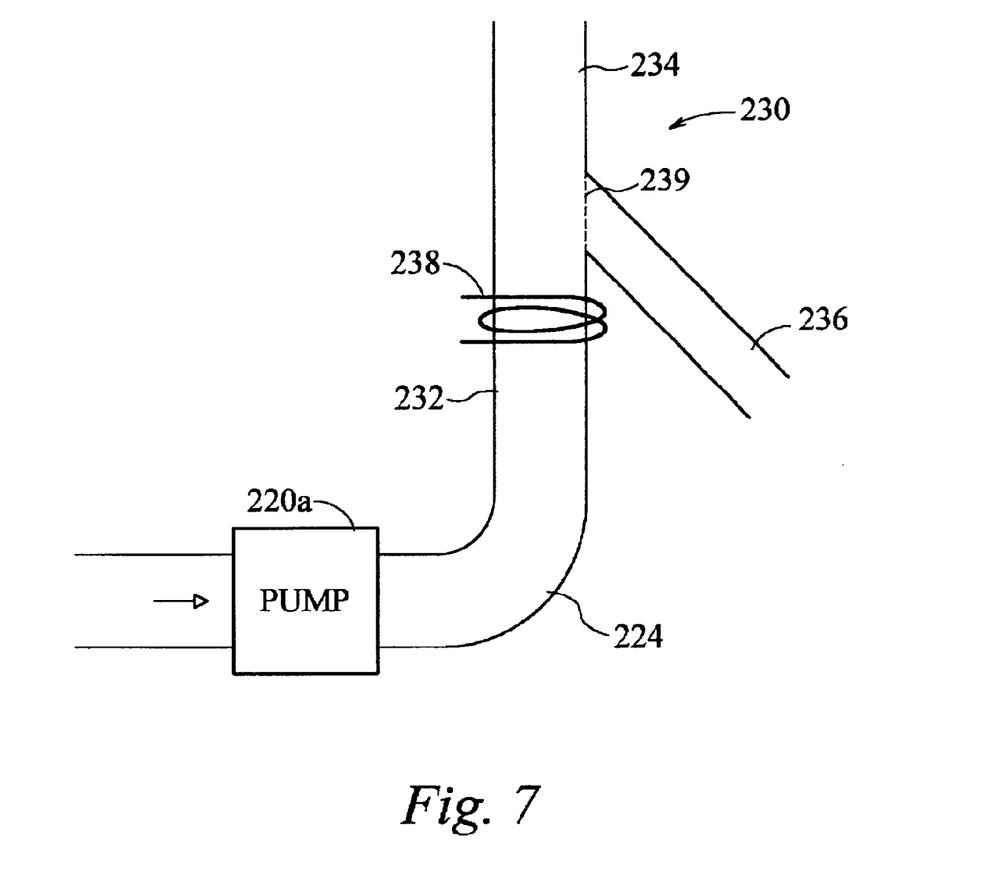
FIG. 7 shows diagrammatically in greater detail the debubbler employed in the embodiment.

The debubbler of the embodiment will now be described in greater detail with reference to FIG. 7, which shows the peristaltic pump 220a and connecting pipe 224 as previously described. Connecting pipe 224 thereafter extends into an upwardly directed vertical section 232. From this section 232 branches a downward angled fluid communication pipe 236 which preferably subtends an angle of between 20° to 70°, more preferably 30° to 45°. The interface portion between the downward angled fluid pipe 236 and vertical pipe 238 is preferable rounded. Vertical pipe 238 extends into a gas exhaust section 234 which passes to the outside of the cartridge 200. By maintaining a fluid level above the interface to angled pipe 236 (shown diagrammatically by meniscus 235) the debubbler is effective to allow the exhaust of excess air from the fluid sample to the atmosphere.

In the embodiment, a heater coil 238 is provided, under the control of the microprocessor 280, which surrounds the vertical pipe 232 and is effective to heat the fluid contained therein so as to further promote the discharge of dissolved air, this being a preferable feature. Preferably, the heater is effective to cause a temperature rise in the fluid of between 10 to 60 degrees centigrade, typically to produce an end temperature of about 70 degrees centigrade. A capillary trap 239 is preferably provided to trap small bubbles. In a modification a thermocouple may be provided in the region of the debubbler to provide feedback to the microprocessor in respect of the temperature achieved. In a further modification, the microprocessor may adjust the amount of heat provided in response to analysis data from previous samples so as to reduce the possibility of the heater causing the decomposition of material intended to be the subject of analysis. Heat may be supplied from a heating element on the main body 100.

Once the sample has passed from the debubbler 230 along downward pipe 236 it proceeds to the main body for analysis via needle interface 300. This needle interface comprises a needle holder from which protrudes needle 320. As previously described, these needles are protected by a resealable seal when the cartridge 200 is detached from the main unit 100. In use, each of the needles 320 penetrates from the cartridge 200 and is received by a needle receiver 310 on the main unit 100. The needle contains an outlet adjacent to its end for the discharge of fluid which is passed into the needle receiver 310. All fluid exchange between the main unit 100 and the cartridge 200 is achieved using a needle interface and the description of such interface, will not, therefore, be repeated in detail.

The cartridge 200 also contains chemical reagents for use by the analysis wafer. These are contained in plural storage bags 240, there being twelve such bags in the preferred embodiment, only three of which 240a, 240b, 240c are shown in FIG. 6. Reagents are provided from the bags under gravitational feed to the analysis wafer 110 inside the main body, each feed having its associated piping and needle interface. Typically the reagent bags will have a capacity of between 1 and 100 cubic centimeters ($cm^3$).

Also provided is a waste storage bag 265 for the storage of toxic waste output from the analysis wafer in order to allow such waste to be held in isolation for subsequent disposal upon replacement of the cartridge. In the embodiment, the waste bag has a capacity of 50 to 500 $cm^3$. In a modification, plural toxic waste bags may be provided so as to provide increased storage for such waste or so as to prevent the mixing of different types of such toxic waste.

The reagent bags 240 and waste bag 265 will now be described in further detail. These bags are held substantially vertically from a rigid (typically metal) support 241 so as to achieve at least partial gravity feed to the analysis wafer 110. The bags are positioned in a water reservoir 245 which substantially maintains hydrostatic pressure of the reagent within its bag. An overflow 247 such that the water level, and hence the hydrostatic pressure, is maintained substantially constant A preferable feature of the embodiment is the facility to maintain the certain of the reagent bags (in the illustrated embodiment bags 240b, 240c) at predetermined temperatures. Considering reagent bag 240b as an example, it is substantially surrounded by thermally conductive layer 241b which is itself substantially surrounded by thermally insulating layer 242b such as to prevent dissipation of heat to the water reservoir 245 or any other parts of the cartridge 200. The two layers 241b, 242b are flexible so that the feature of hydrostatic pressure equalisation provided by the water reservoir 245 is maintained. The thermally conductive layer 241 b is connected via thermal pathway 290 to thermal interface 340 and thereafter to the heater cooler 120 positioned in the main unit. Reagent container 240c is arranged in a similar manner.

By way of example, such reagents may comprise ammonia to be maintained at a temperature of 4° Celsius. A biological reactor may be maintained at 37 degrees Celsius to keep the micro-organisms viable.

In an unshown modification, a thermocouple or similar temperature sensing device may be positioned in contact with the thermally conductive surrounding layer or internal to the bag in contact with the reagent. In such a modification, the thermocouple would proved feedback to the cartridge microprocessor 280 for onward transmission to the main body microprocessor 150, thus allowing the operation of heater/cooling unit 120 to be adjusted accordingly so as to maintain the reagent at the desired temperature.

As previously stated, ordinary waste from the analysis wafer 110 is expelled from the buoy. Such waste passes from the analysis wafer 110 to the cartridge 200 via a needle interface 301 to a second chamber of the peristaltic pump 220b (which is shown diagrammatically as a separate unit in FIG. 6). This pumps the waste to the waste output 260 where it is discharged from the unit via waste orifice 272.

As previously mentioned, there is a third intermediate category of waste which may be discharged from the analysis wafer 110. This passes into the cartridge 200 and is discharged into the water space 245 thus assisting in the maintenance of hydrostatic pressure which might be affected by the depletion of reagents from the reagent containers 240. Although it will be appreciated that the provision of the overflow 247 from the water space 245 leads to the possibility of such intermediate waste being discharged from the buoy, it will further be understood that the effects of dilution by the water will render such waste substantially harmless. The waste may be aerated.

In the embodiment an additional analysis chamber is provided in the cartridge, namely biological oxygen sensor 250. The composition of this sensor is such that it has a finite lifetime and hence it is convenient for it to be provided in the cartridge 200. Data from the biological oxygen sensor 250 is passed along data bus 252 (only part of which is shown) to microprocessor 280 for subsequent storage and analysis.

Figure 8:
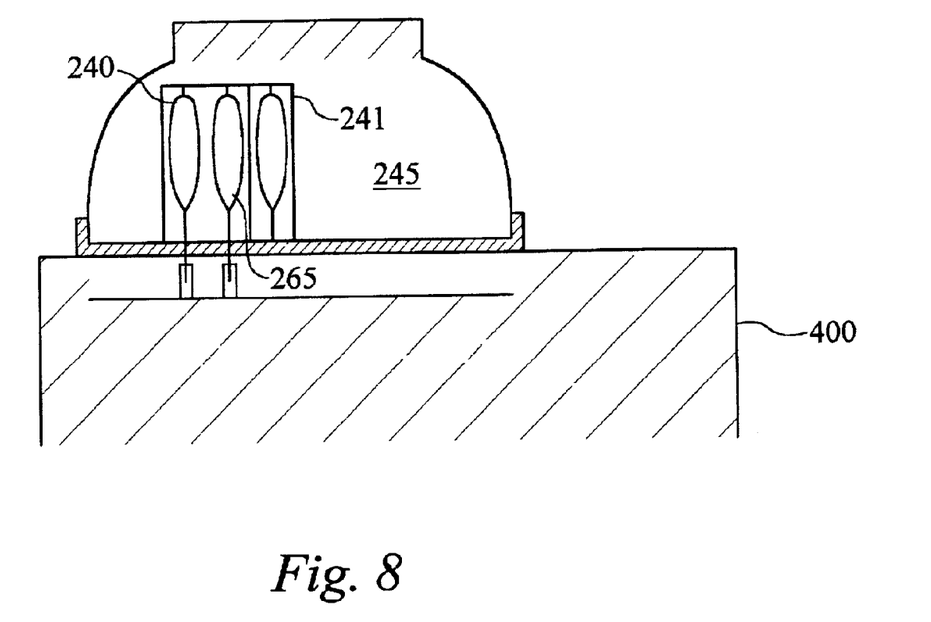
FIG. 8 shows diagrammatically the replenishment method in the embodiment of the invention.

A method of replenishment and renewal of the cartridge 200 will now be described. Once the cartridge has been detached from the unit, which may occur in situ, it is passed to the manufacturer or a licensee for recycling. The recycler may extract the non-volatile RAM 282 and pass this or a copy of the analysis data recorded thereon to the user. The recycler may use additional date stored on the non-volatile RAM such as the quantity of each reagent used; the overall power consumption of the cartridge and the like for statistical or development purposes. The contents of the waste bag 265 will be disposed of in any known conventional manner.

The empty or partially empty reagent bags 240 may be disposed of or merely emptied. The reagent may be reused or more likely discarded. The biological oxygen sensor 250 will be renewed. Other parts of the cartridge such as the pump 220 the needle interfaces 300, 301 and 322 will be inspected for wear and cleaned, reconditioned or replaced as necessary.

The cartridge 200 will then be attached to replenishment unit 400, which includes an interface part 410 arranged to mate with the cartridge 200.

The replenishment unit includes a vacuum pump (not shown) which is switchable so as to extract the air from each of the empty reagent bags 240 and the waste bag 265 in turn so as to create a vacuum therein. The desired reagent is then pumped into the bag so as to fill it. In this manner, an air tight environment is maintained in each bag so as to prevent subsequent oxidation of the reagent. A suitable quantity of water is pumped into the cartridge via a further fluid interface (not shown) so as to fill the water reservoir 245. It should be noted that a septum which seals will preferably be connected between the needle connected to the waste bag and the waste bag itself such that the vacuum in the waste bag is maintained until the cartridge 200 is interfaced with the main unit 100.

In a modification a battery may be provided in the cartridge so as to provide power for the units therein. In a further modification, the battery (or a fuel cell) would also provide power to the buoy in which case the power unit 130 of the above embodiment would be excluded. In such a case a small back-up battery could be provided in the main unit to sustain basic operations whilst a cartridge was not connected. The back-up battery could be rechargeable so as to be maintained by the battery in the cartridge.

In a further modification, analysis data could be provided to a wireless link such as a radio or infra red link for transmission back to a base station for instantaneous analysis. It is preferred that such a modification would be provided in combination with the above described internal battery modification so as to result in a wireless unit.

In a further modification, the ROM 286 provided in the cartridge will include a list of the provided reagents together with data indicative of a desired storage temperature. On replacement of a cartridge, this data would be provided to the microprocessor 150 in the main unit to enable it to instruct heating/cooling unit 120 accordingly.

In the above described embodiment, a biological oxygen sensor was described as an example of a sensor requiring replenishment and/or renewal and/or maintenance. This is only one of a number of such sensors which could be provided in the cartridge 200 either solely or in combination.

In a further modification, the cartridge will include sensors to maintain a measurement of the quantities of reagent or waste in each bag. Such data would be read by the microprocessor 280 in the cartridge 200 and could subsequently provide a warning of the imminent necessity of cartridge replacement and when actual replacement was necessary. A further lifetime sensor could be provided associated with any analysis unit provided in the cartridge 200 to give a similar indication.

Although a particularly useful tool for analysis of waste water, the analysis buoy may be adapted for analysis of other fluids, slurries or suspensions, for example in a food processing plant or brewery. The buoy is preferably buoyant and arranged to float in the fluid to be analysed at a desired level, but a housing which is not necessarily buoyant may be used in place of a buoy, if suitable support is provided.

Other modifications will be apparent to those skilled in the art. Features, particularly the preferred features identified above, may be provided independently or in any combination. The appended abstract is incorporated herein by reference.

We claim:

1. Analysis apparatus comprising a main body part and a cartridge part:

the main body part being adapted for positioning in a fluid to be analyzed and including analysis means; and the cartridge part including means for extracting a sample from the fluid; means for storing at least one reagent and transfer means for transferring the sample and the at least one reagent to the analysis means so as to permit analysis of the sample, said transfer means comprising a needle situated on the said part and a corresponding needle receiving means situated on the other said part.

2. Apparatus according to claim 1 wherein said transfer means for transferring the sample and the at least one reagent to the analysis means comprises a said needle comprising an associated needle portion situated on the cartridge part and said main body part further comprises a said needle receiving means comprising a corresponding needle receiving portion and an associated communication pathway to the analysis means.

3. Apparatus according to claim 2 wherein said cartridge part further comprises a baseplate having a resealable aperture, said baseplate being movable between a non-mated position where said needle portion is covered by the seal of said resealable aperture and a mated position where said parts are mated together and where said needle penetrates through said resealable aperture.

4. Apparatus according to claim 3 further comprising means for preventing said baseplate moving between the mated position and the non-mated position unless said first and second means are at least partially mated.

5. Apparatus according to claim 1 wherein each of said means for storing at least one reagent comprises a flexible bag for each of said reagents.

6. Apparatus according to claim 5 wherein said cartridge part further comprises a chamber for the storage of water and wherein said flexible bags are situated within said chamber.

7. Apparatus according to claim 6 wherein said chamber comprises means for maintaining the water within the storage chamber at a predetermined level.

8. Apparatus according to claim 6 wherein said main unit body part further comprises means for passing waste to said cartridge part and said cartridge part is adapted to discharge the waste into the water storing chamber.

9. Apparatus according to claim 1 wherein said main body part comprises temperature control means and means for the thermal transfer to the output of said temperature control means to an thermal interface with the cartridge means and wherein said cartridge part comprises thermal interface means and means for providing a thermal pathway to a thermally conductive material surrounding at least one of the reagent storing means so as to maintain the reagent at a predetermined temperature.

10. Apparatus according to claim 9 wherein said temperature control means is adapted to cool the reagent.

11. Apparatus according to claim 1 wherein said main body part further comprises a microprocessor for controlling the analysis means and receiving data indicative of the results of said analysis and said cartridge part further comprises non-volatile memory for storing said results data.

12. Apparatus according to claim 1 wherein said cartridge part further comprises analysis means.

13. Apparatus according to claim 12 wherein said analysis means provided in said cartridge part comprises a biological oxygen sensor.

14. Apparatus according to claim 12 wherein said main body part further comprises means for directing a sample to the analysis means of the cartridge part.

15. Apparatus according to claim 1 wherein said cartridge part further comprises means for reducing the content of dissolved air in the sample.

16. Apparatus according to claim 15 wherein said means for reducing the content of dissolved air in the sample comprises an upwardly vertically extending input pipe the upper end of which is vented to the atmosphere and a downwardly angled output pipe in fluid communication with said input pipe.

17. Apparatus according to claim 16 further comprising a heater in the region of the connection between said input pipe and said output pipe.

18. Apparatus comprising a main body part and a cartridge part which, in use, are mated wherein:

said main body part is adapted for positioning in a fluid to be analyzed and includes analysis means; and said cartridge part comprises means for extracting a sample from the fluid;

wherein said apparatus comprises means for transferring the sample from said extraction means to said analysis means so as to permit analysis of the sample, said means comprising a needle situated on the cartridge part and corresponding needle receiving means situated on the main body part.

19. Apparatus according to claim 18 wherein said cartridge part further comprises a baseplate having a resealable aperture, said baseplate being movable between a non-mated position where said needle portion is covered by the seal of said resealable aperture and a mated position where said main body part and said cartridge part are mated together and where said needle penetrates through said resealable aperture.

20. Apparatus according to claim 19 further providing means for preventing the penetration of said needle through said aperture until said cartridge part and said main body part are at least partially mated together.

21. Apparatus according to claim 18 wherein interfacing portions of said cartridge part and said main body part are keyed.

22. Apparatus according to claim 1 wherein said main body part further comprises a rotational motor and associated coupling means and said cartridge part comprises a pump adapted to be driven by said rotational motor via said coupling means, said pump being adapted to extract a sample from the fluid.

23. An analysis device comprising a main body part and a cartridge part which, in use, are mated wherein:

said main body part is adapted for positioning in a fluid to be analyzed and includes analysis means; and said cartridge part comprises means for the storage of waste material after analysis and wherein said device comprises transfer means for transferring the waste from said analysis means to said storage means, and said transfer means comprises a needle situated on one said part and a corresponding needle receiving means situated on the other said part.

24. An analysis device according to claim 23 wherein said means for transferring the waste from said analysis means to said storage means comprises a needle situate on the cartridge part and corresponding needle receiving means situated on the main body part.

25. An analysis apparatus comprising a main body part and a cartridge part, which, in use, are mated to form an integrated unit and which, when mated, are separable from each other, wherein the cartridge part includes means for extracting a sample from the fluid, a means for storing at least one reagent, a means for analyzing the fluid sample, a means for mixing the fluid sample with a respective portion of the stored reagent, a means for analyzing the fluid sample after reacting with the reagent, and pumps for transporting the sample and reagents; and the main body part comprising motors for driving the pumps in the cartridge, and the main body part further being adapted for positioning in a fluid to be analyzed.

26. An analysis buoy according to claim 25 wherein said analysis means for analyzing said fluid comprises a biological oxygen sensor.

27. Apparatus according to claim 1, wherein the cartridge part and the main body part include an interface therebetween, wherein a liquid to be analysed is contained within th cartridge part and wherein the interface between the main body part and the cartridge part passes no liquid.

28. Apparatus according to claim 27, wherein the interface comprises means for transferring electrical power and/or means for transferring mechanical power between the cartridge part and the main body part.

29. Apparatus according to claim 27, wherein the interface comprises means for transferring data to or from the cartridge part.

30. Apparatus according to claim 25 further comprising a releasable interlocking connection between said main body part and said cartridge part for releasably interlocking said main body part and said cartridge part together.

31. Apparatus according to claim 25 further comprising transfer means, comprising a needle and a needle receiving means, for transferring a reagent to the analysis means.

32. Apparatus according to claim 24, wherein the cartridge part and the main body part include an interface therebetween, wherein a liquid to be analysed is contained within the cartridge part and wherein the interface between the main body part and the cartridge part passes no liquid.

33. Apparatus according to claim 32, wherein the interface comprises means for transferring electrical power and/or means for transferring mechanical power between the cartridge part and the main body part.

34. Apparatus according to claim 32 wherein the interface comprises means for transferring data to or from the cartridge part.

* * * * *